United States Patent [19]
Durham

[11] Patent Number: 6,074,392
[45] Date of Patent: Jun. 13, 2000

[54] METHOD AND DEVICES FOR USE IN BONE FIXATION PROCEDURES

[76] Inventor: Alfred A. Durham, 2110 Carolina Ave., SW., Roanoke, Va. 24014

[21] Appl. No.: 09/145,160

[22] Filed: Sep. 1, 1998

[51] Int. Cl.[7] .................................................. A61F 5/04
[52] U.S. Cl. ............................................. 606/67; 606/62
[58] Field of Search ................................ 606/1, 60, 62, 606/72, 86, 67

[56] References Cited

U.S. PATENT DOCUMENTS

| | | | |
|---|---|---|---|
| 4,712,541 | 12/1987 | Harder et al. | 606/67 |
| 5,013,314 | 5/1991 | Fircia et al. | 606/67 |
| 5,135,527 | 8/1992 | Ender | 606/62 |
| 5,624,447 | 4/1997 | Myers . | |

Primary Examiner—Michael Buiz
Assistant Examiner—William W. Lewis
Attorney, Agent, or Firm—Larson & Taylor

[57] ABSTRACT

A curved guide or fixation pin is provided for use in the fixation of fractured bones. In one embodiment, a pin guide device is used to locate the pin at the desired entry point on the bone and the pin is tapped or hammered into place. With the guide device removed, the pin is driven further into the bone and a flexible reamer device, which is placed over the pin and which uses the pin as guide, is used to ream out the path defined by pin so as to prepare the bone for a intermedullary rod. The curvature of the pin assists in ensuring that the path of the pin connects to the medullary canal. In another embodiment, the curved pin has an enlarged proximal head and a two piece pin guide device is used which is disassembled after the pin initially penetrates the bone so as to permit the pin to be driven home. A self-retaining protective retractor device provides soft tissue protection during the reaming operation and eliminates the need for medical personnel to hold the retractor device.

27 Claims, 5 Drawing Sheets

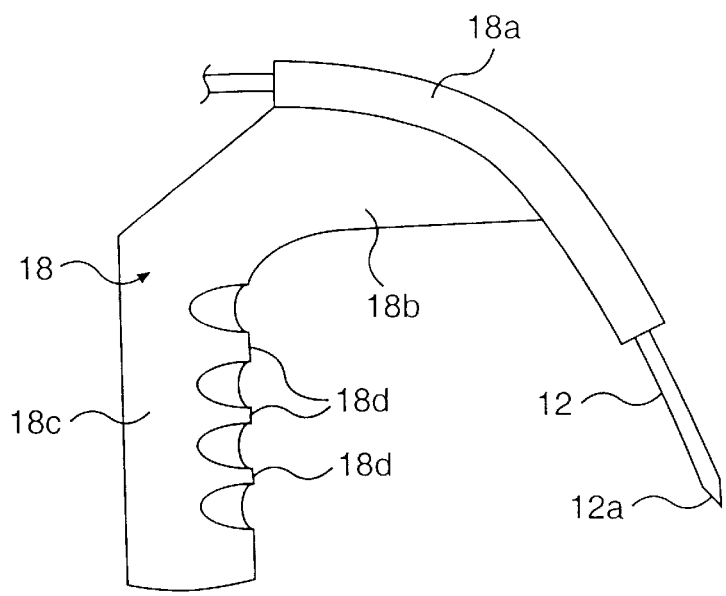
FIG. 3
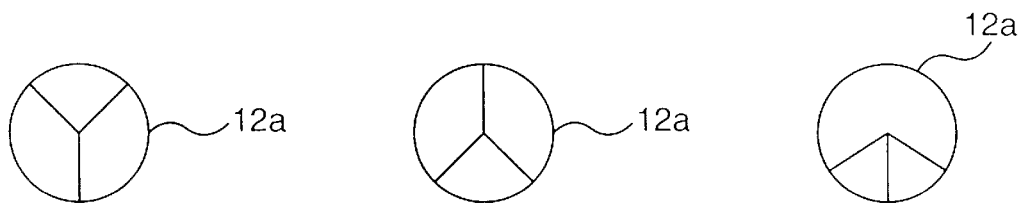
FIG. 5 (a)    FIG. 5 (b)    FIG. 5 (c)
FIG. 5 (d)    FIG. 5 (e)

METHOD AND DEVICES FOR USE IN BONE FIXATION PROCEDURES

FIELD OF THE INVENTION

The present invention relates to methods and devices for placing intramedullary rods, fixation pins and the like in the bones of patient and to related methods and devices useful in such procedures.

BACKGROUND OF THE INVENTION

A common method of repairing bone fractures involves the insertion of fracture rods, i.e., intramedullary rods or "nails," fixation pins and the like, into the intermedullary canal of the bone. However, it can be difficult to correctly position the entry point or hole relative to the intermedullary canal and accurate positioning of the entry point is critical to proper intermedullary "nailing."

This problem can perhaps be better understood by reference to FIG. 1 wherein a portion of the pelvis is indicated at P, a long bone is indicated at B and the "soft" bone at the top of the long bone B is indicated at S. The soft bone S must be penetrated in order to provide access to the medullary canal MC to enable placement of an intermedullary rod or "nail" along this canal. In FIG. 1, a conventional reamer R is shown driving a conventional straight drill or associated straight drill pin into the soft bone S to create an entry point for the rod. The entry point for the insertion of the rod is often hidden by muscle and hard to access because of the soft tissue. It will be seen in FIG. 1 that a straight reamer or drill can produce an entry point EP that is substantially offset from the bone axis and the axis of the medullary canal MC so that as the straight drill continues along its path the drill can overshoot the canal and problems can then be created in attempting to insert a straight fracture rod.

As discussed below, in one embodiment of the invention, the guide pin of the invention is used in combination with an entry guide tool. A surgical tool guide and entry hole positioner of interest is disclosed in U.S. Pat. No. 5,642,447 (Myers). In one embodiment, the tool guide disclosed in Myers patent includes a guide sleeve which is curved, rather than straight as in the other embodiments, and is adapted for use with flexible reamers. According to the Myers patent, the reamers can be used without changing sleeves and, in this regard, as stated in the patent, the tips of the flexible reamer are merely enlarged incrementally so as to ream the intramedullary canal to a size large enough to receive the fracture fixation rod (nail).

As is also discussed below, the invention is also concerned with an improved protective retractor device which is useful during reaming operations. Prior art protective retractor devices are also discussed briefly hereinbelow.

SUMMARY OF THE INVENTION

In accordance with one aspect of the invention, an improved guide or fixation pin is provided for use in fixation of a fractured bone, the pin comprising a curved pin member of a radius of curvature between one and seven inches, and including a proximal end, and a sharp distal end adapted to be driven into bone to be fixated by repeated impacts on the proximal end of the curved pin member. As discussed below, the curvature of the pin enables the pin to, e.g., follow a desired curved path providing entry to the medullary canal of a long bone.

Preferably, the curved pin member is tapered over at least a portion of the length thereof between the proximal and distal ends. Advantageously, the curved pin member includes fluting at the proximal end thereof. For some applications discussed below, the pin member preferably includes an enlarged head at the proximal end thereof.

In accordance with an important feature of this aspect of the invention, the sharp distal end can take a number of different forms useful in different applications of the curved pin member. In one embodiment, the sharp distal end of the curved pin member is symmetrical in cross section and has a symmetrically disposed tip. In another embodiment wherein the pin is adapted for use, e.g., as guide pin for a reamer, the curved pin member has an inner radius shorter than the outer radius thereof, and the sharp distal end includes an inwardly oriented asymmetrical tip, i.e., a tip located closer to the inner radius than the outer radius, so that the path followed by the pin member in response to repeated impacts on the proximal end thereof tends to increase in curvature during the travel of the pin member. In this embodiment, the pin member preferably has a radius of curvature of about six or seven inches, and is particularly adapted for use as guide pin for reamer in a surgical placement of an intermedullary rod. In a further embodiment of this aspect of the invention wherein the curved pin member has an inner radius shorter than the outer radius, the sharp distal end includes an outwardly oriented asymmetrical, i.e., a tip located closer to the outer radius that the inner radius so that the path followed by the pin member tends to straighten out in response to repeated impacts on the proximal end thereof. In this embodiment, the pin member preferably has a radius of curvature of from about one to three inches, advantageously has an enlarged proximal end portion or head, and is beneficially adapted for use in the fixation of small bones.

In accordance with a further aspect of the invention, a method is provided for fixating a small bone having fracture, the method comprising: providing a curved pin element having a radius of curvature of between one and three inches; and driving the pin element into the small bone to provide fixation of the fracture.

In this embodiment, pin element includes an enlarged proximal end or head portion and the pin element is driven into the bone by repeated impacts on this head portion. Preferably, the method further comprises using a pin guide device having a hollow curved pin guide portion in placing the pin element at a desired entry point the small bone. In an advantageous implementation, at least the pin guide portion of the guide device comprises separable portions and the method further comprises placing the distal end of the pin guide portion against the small bone at the desired entry point, inserting the curved pin element through the pin guide portion and hammering the pin element into the bone, separating the separable portions of the guide device to free the pin from the device, and thereafter hammering the pin further into the bone to provide the desired fixation.

In accordance with yet another aspect of the invention, a method is provided for preparing a fractured bone of a patient for the introduction of an intermedullary rod for fixating the bone, the method comprising: creating an entry incision through soft tissue adjacent to an end portion of the fractured bone into which intermedullary rod is to be inserted; driving a curved guide pin into the bone so that the guide pin at least penetrates into the medullary canal; placing a protective retractor device over an area of the patient adjacent to the bone; disposing a flexible reamer element over the curved guide pin; and, using the curved guide pin as a guide, reaming out the bone along the length of the guide pin to create a reamed opening into the medullary canal.

Preferably, the method further comprises capturing the guide pin with the flexible reamer and, thereafter, removing the reamer with the guide pin captured thereby.

Advantageously, the method further comprises using a pin guide device to guide the curved guide pin to a desired entry point on the bone prior to driving the pin into bone. The pin guide device advantageously includes a curved guide portion having a distal end, and the method further comprises inserting the curved guide pin through the curved guide portion and hammering the pin into the bone, removing the guide device and hammering the pin further into the bone in preparation for the reamer.

Advantageously, the placement of the protective retractor device includes placing a protective pad portion of the retractor device over said area, securing a distal end of the retractor device to the bone, and using a tensioning arm of the retractor device to further secure the device in place. The step of using of the tensioning arm to secure the retractor device in place preferably includes engaging the tissue at one end of the entry incision with one end of the tensioning arm and also clamping the pad to the tensioning arm.

In accordance with still anther aspect of the invention, a protective retractor device is provided for use during surgical procedures involving fixation of a bone, the device comprising: a protective pad including a cover portion adapted to cover an area of the skin of a patent adjacent to an entry incision providing access to the bone to be fixated and an end portion including affixing means for affixing the pad to the bone; and an elongate tensioning member adapted, in use, to underlie the cover portion of the protective pad and including position fixing means at one end thereof for engaging tissue adjacent one end of the entry incision and pad engaging means for engaging the cover portion of the protective pad and fixing the position of the pad.

Advantageously, the cover portion is generally oval in shape. The affixing means at the end portion of the protective pad preferring includes at least one spike element for penetrating the bone to provide fixing of the protective pad in place.

Advantageously, the protective pad includes a longitudinally extending slot therein and the pad engaging means of said tensioning member includes a clamping element which, in use, extends through the slot and engages the protective pad. Preferably, the slot has a keyhole shape including an enlarged opening at one end and the clamping element includes an enlarged head portion sized to fit through said enlarged opening and to be captured with the remainder of the slot. The tensioning member preferably includes adjustment means for enabling adjustment of the position of the clamping element therealong. Advantageously, the clamping element includes a threaded end, and the adjustment means comprises a plurality of screw holes included in the tensioning member at longitudinally spaced locations therealong.

The position fixing means of the tensioning member preferably includes a hook element for, in use, entering into the incision at said one end of the incision.

Other features and advantages of the invention will be set forth in, or apparent from, the following detailed description of preferred embodiments of the invention.

BRIEF DESCRIPTION OF THE DRAWINGS

FIG. 3 is a side elevational view of a guide pin and pin guide device in accordance with a further aspect of the invention;

FIGS. 5(a) to 5(e) are end elevational views respectively showing different tip embodiments of the guide pin of the invention;

DESCRIPTION OF THE PREFERRED EMBODIMENTS

Figure 1:
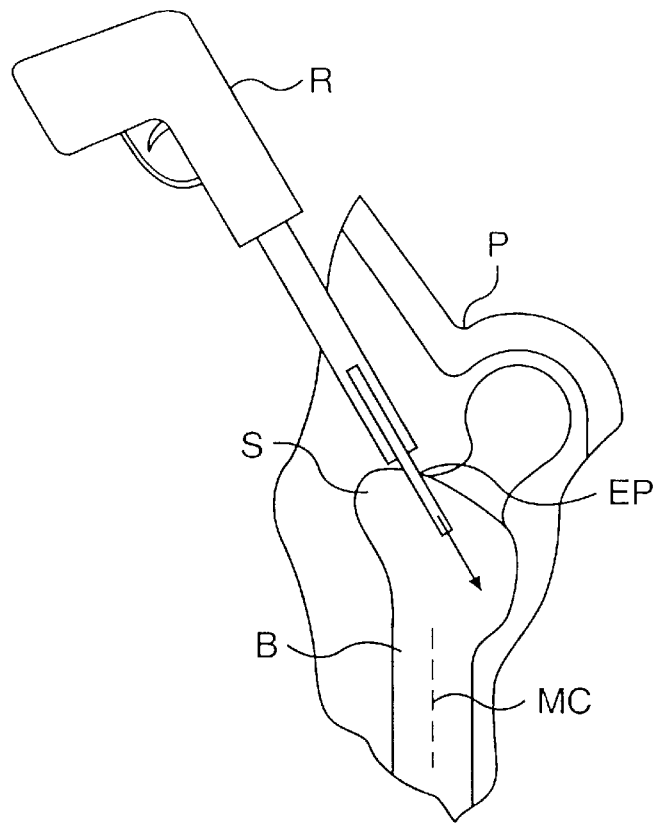
FIG. 1 is, as described above, a schematic representation of a prior art reaming operation.
Figure 2:
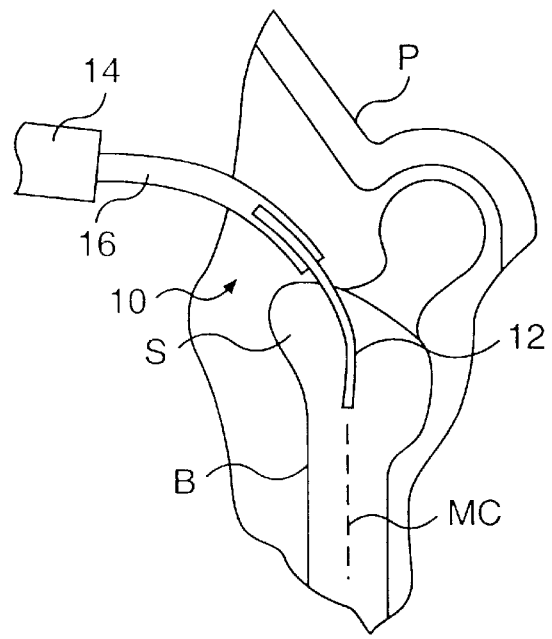
FIG. 2 is a side elevational view partially in section, similar to that of FIG. 1, showing a reaming operation in accordance with the invention, using a guide pin in accordance with the invention.

Referring to FIG. 2, a view similar to FIG. 1 is provided wherein there is shown a drilling assembly or arrangement in accordance with a first preferred embodiment of the invention. A key element of the drilling assembly, which is generally denoted 10, is a curved guide pin 12. The curvature of the pin 12 is preset and fixed and the pin 12 is inserted into the bone to provide a guide path for a drill or reamer so as to enable insertion of a fixation device such as an intermedullary rod or nail or, alternatively, to serve as the fixation device itself, in the case of small bones. In the embodiment of FIG. 2, a flexible drill or reamer is shown at 14 which includes a hollow flexible drill or reamer element 16 in which the curved pin 12 is received and which bends or flexes so to accommodate the curvature of the pin. Flexible drill or reamer 14 is itself conventional. The overall operation of this embodiment of the invention is described below in connection with FIGS. 4(c) and 4(d).

In further embodiment of the invention shown in FIG. 3, the curved guide pin 12 is used with a pin entry guide device or pin guide device, denoted 18, having a curved, hollow pin guide portion 18a supported by a support member 18b on a handle grip 18c with gripping ridges 18d. The curvature of pin guide portion 18a is such as to accommodate that of the curved pin 12, and the length thereof is less than that of pin 12 so that the pin 12 can be inserted through the guide portion 18a and then driven into the bone or otherwise manipulated.

Figure 4:
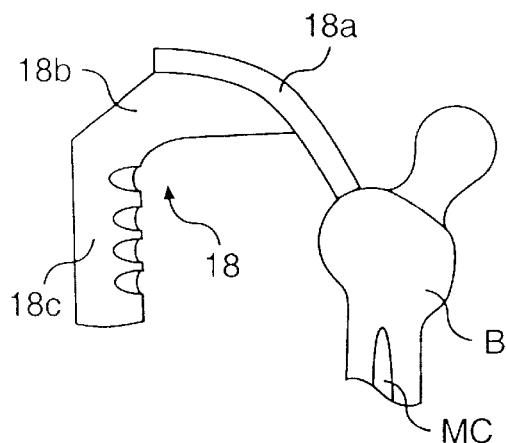
FIGS. 4(a) to 4(d) are schematic representations illustrating sequential steps in a method in accordance with one embodiment of the invention.
Figure 4:
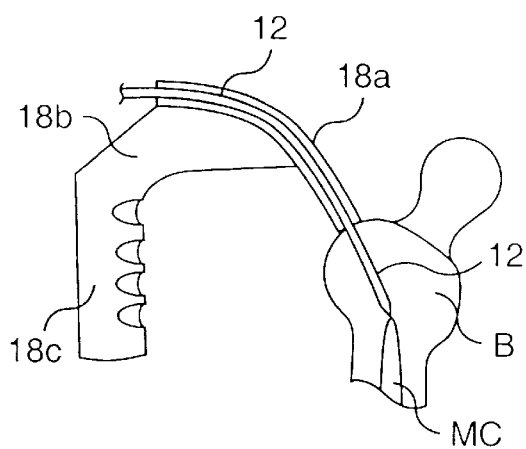
Figure 4:
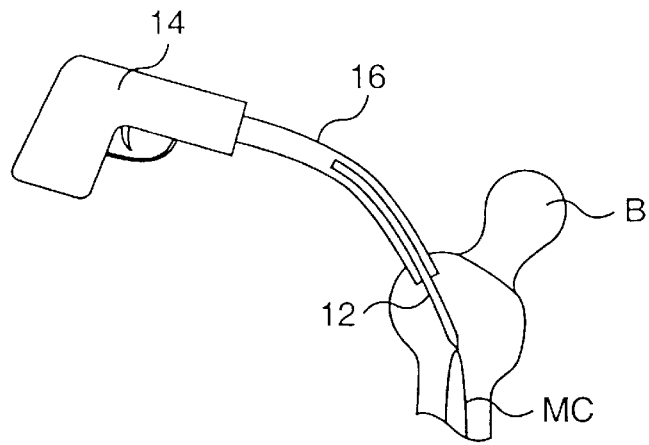
Figure 4:
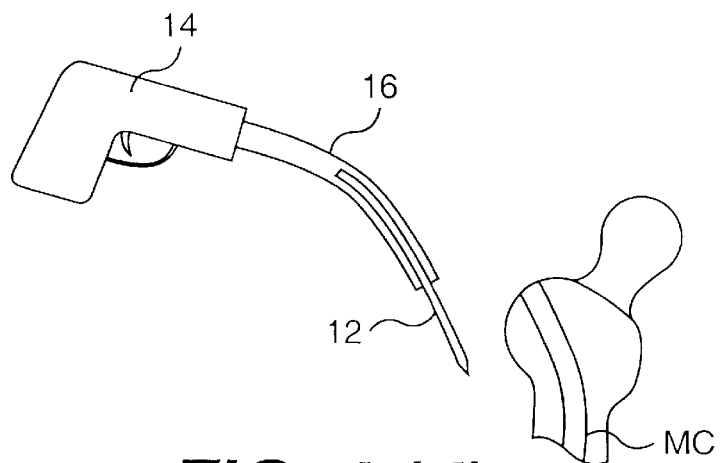

Before the details of construction of different embodiments of the guide pin 12 are considered, reference is made to FIGS. 4(a) to 4(c), which show steps in the use of the various devices shown in FIGS. 2 and 3. First, as shown in FIG. 4(a), a pin guide device 18, corresponding to that shown in FIG. 3 and having a corresponding curved pin guide portion 18a, is positioned such that the distal end of portion 18a is disposed at the desired entry point of the long bone B to be rodded. This positioning of guide portion 18a at a suitable entry point can be accomplished with the assistance of X-rays or by direct visualization of the site.

Next, as shown in FIG. 4(b), using curved guide portion 1 8a, the curved guide pin or guide wire 12 is aligned with the longitudinal axis of long bone B. The curvature of pin 12 will cause it to naturally follow a path which lines up with this axis. The pin 12 is hammered or otherwise driven into the bone B with gentle taps of a hammer or like on the proximal end thereof In this way, the guide pin or wire 12 is made to follow, due to its shape, a curved path or course through the soft bone into the upper end of the medullary canal MC of bone B.

In the next step, illustrated in FIG. 4(c), pin guide device 18 is removed and a short tip flexible reamer 14, corresponding to that shown in FIG. 2, is placed over the guide pin 12. The reamer 14 is used to drill into the bone B over the length of pin 12. When this is accomplished, the reamer 14 is then stopped. The reamer 14 captures the pin 12 in the flexible drilling or reamer portion 16, as shown in FIG. 4(d), and thus pin 12 can be removed from the bone B when the reamer 14 is removed.

As shown in FIG. 3, pin or wire 12 has a pointed distal end or tip 12a, and referring to FIGS. 5(a) to 5(e), different embodiments of that tip are shown. In FIG. 5(a), tip 12a is symmetrical in cross section and in tip location. More specifically, regarding the latter, the point of the spade tip is centered and is formed by three equal converging planes, as shown. In FIG. 5(b), tip 12a is also symmetrical in cross section but the point location is asymmetrical, i.e., the tip point is located on the inner aspect of the tip. In FIG. 5(c), the tip cross section is asymmetrical and the point location is symmetrical while in FIG. 5(d), both the tip cross section and the point location are asymmetrical. Finally, in FIG. 5(e), the cross section is symmetrical and point location is on the outer aspect of the tip.

In the embodiments in FIGS. 5(b), 5(c), and 5(d), each of the pins 12 has less mass on the inside radius of curvature and therefore these pins tend to bend into the curvature and more easily provide access to the medullary canal for the reamer. In the embodiment of FIG. 5(e), wherein the least amount of mass is on the outer radius of the pin 12, the pin tends to straighten when leaving the pin guide 18a and can be used to as a definitive fixation element. In other words, while the initial path of such a pin is curved, the increased mass on the outer curvature will cause the pin to tend to straighten as the pin enters the medullary canal or a small bone. In contrast to the other embodiments, the symmetrical cross section and tip location shown in FIG. 5(a) do not influence the path of the pin 12 through the bone.

Figure 6:
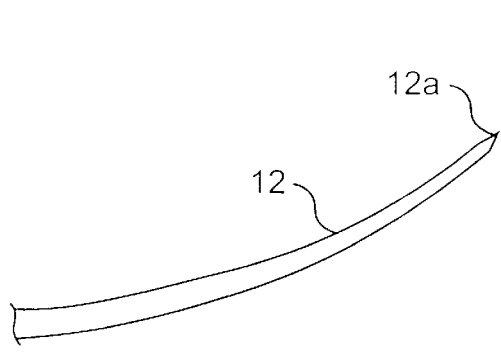
FIGS. 6(a) and 6(b) are side elevational views of two preferred embodiments of the guide pin of the invention.
Figure 6:
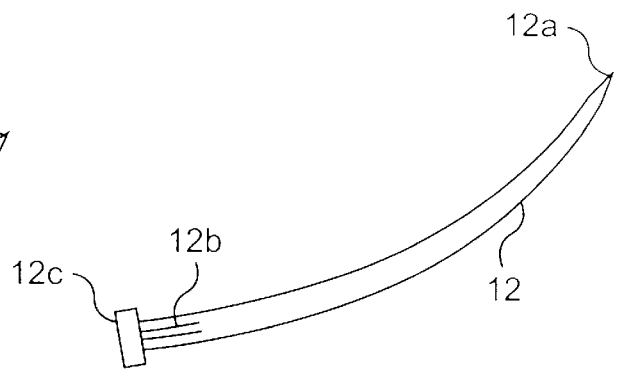

Turning now to some constructional details of preferred embodiments of the guide pin 12, in general, the radius of curvature of pin 12 for long bones should be between about five to eight inches and preferably between about six to seven inches while for small bones the radius of curvature should be between one and four inches and preferably about one to three inches. As shown in FIG. 6(a), in one preferred embodiment, pin 12 is tapered down from the proximal end to the distal end. The thinner cross section distal end provides more flexibility and thus permits this end to more easily follow the medullary canal, while the thicker cross section at the proximal end increases the stiffness of the pin 12 in this region. As shown for the embodiment of FIG. 5(b), fluting, indicated at 12b, can be provided to control rotation of bone fragments. As illustrated, pin 12 can also be provided with a nail head or other enlarged proximal end portion indicated at 12c.

Figure 7:
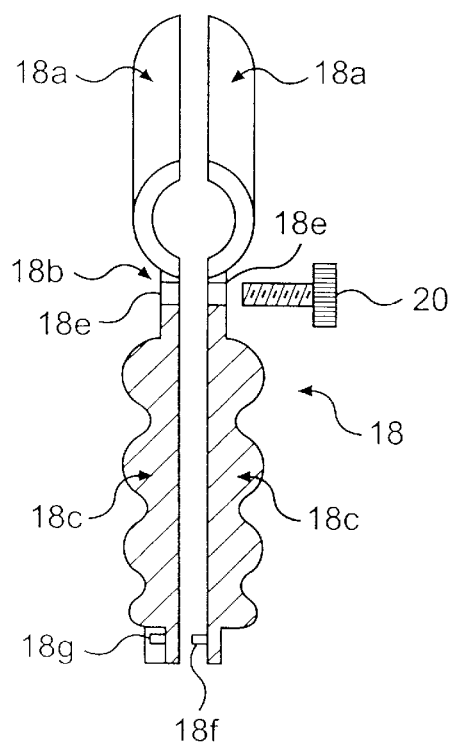
FIG. 7 is an end elevational view, partially broken away, of alternative embodiment of the pin guide device of the invention.

Referring to FIG. 7, there is shown an alternative embodiment of the pin guide device 18 of FIG. 3, which is useful with the pin illustrated in FIG. 6(b), i.e., a pin with an enlarged head portion 12c. In this embodiment, device 18 is similar to that of FIG. 2 but is of a two piece construction. Mating apertures or threaded screw holes 18e provided in the two mating halves of support portion 18b together form a common transverse threaded screw hole for receipt of a thumb screw or connecting screw 20 which locks the two halves together. A projecting pin 18f and cooperating hole 18g are used to assist in properly aligning or mating together the two halves.

Figure 8:
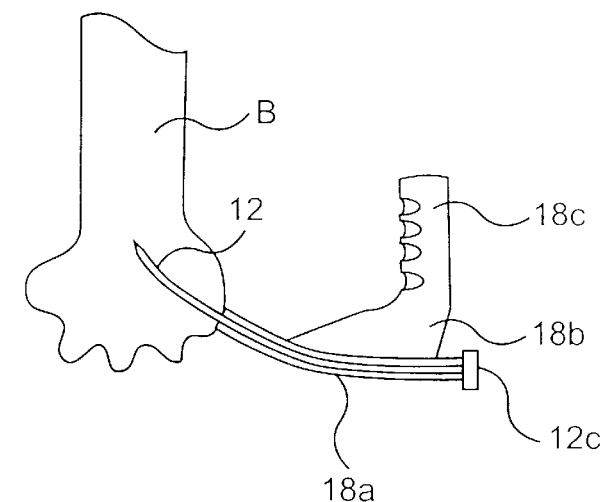
FIGS. 8(a) and 8(b) are schematic representations of a further embodiment of the method of the invention, using the pin guide device of FIG. 7.
Figure 8:
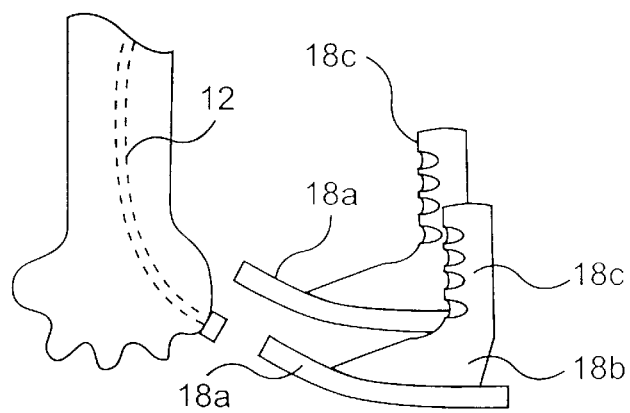

The manner of use of the pin guide device 18 of FIG. 7 is shown schematically in FIGS. 8(a) and 8(b). As illustrated in FIG. 8(a), the device 18 is positioned with the distal end of guide 18a in contact with a bone B. In FIG. 8(a), device 18 is positioned similarly to FIG. 4(a) but in a different orientation. A guide pin 12 with an enlarged head 12c (such as that of FIG. 6(b)) is then inserted in guide portion 18a and gently hammered at the proximal end 12c so that the distal end is driven into the bone B as described above. The pin guide device 18 is then disassembled, by removing connecting screw 20, as shown in FIG. 8(b). Thereafter, using further gentle hammering, the pin 12 is advanced in the bone B to the position illustrated. It is noted that, in general, this embodiment is not used with reamer as described above in connection with FIGS. 4(a) to 4(d), but is rather used where the guide pin 12 is to be left in the bone as a definitive fracture fixation element, and thus is usually used with smaller bones only.

Figure 9:
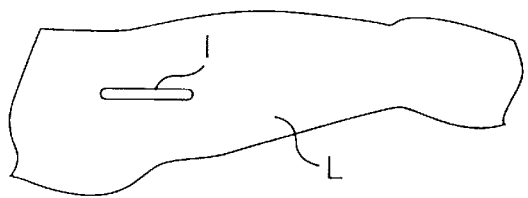
FIG. 9 is a schematic side elevational view of a portion of the body of a patient showing, in a highly schematic manner, an entry incision.
Figure 10:
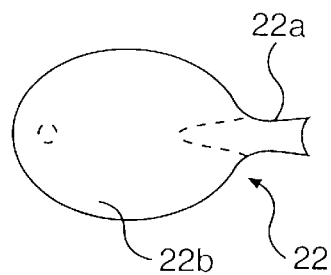
FIG. 10 is a top view of a prior art protective retractor.

Turning now to the other aspect of the invention discussed above, and referring to FIG. 9 by way of background, a typical approach is preparing a patent for the insertion of an intermedullary nail or rod is to provide an incision, indicated at I, in the leg L over the proximal femur. A conventional soft tissue protective retractor, such as that indicated at 22 in FIG. 10, is later used during the reaming operation to protect the patient from flying debris (e.g., blood and bone) produced during such reaming and to retract the soft tissue so as to assist in providing access to bone. Protective retractor 22 includes end portion 22a which extends into the surgical wound and a protective pad portion 22b which, in use, lies flat against the skin of the patient along the side of the patient adjacent to the wound site. Such protective retractors are normally spread from side to side and must be held in place by an assistant. Thus, while the protective function is helpful and necessary, this obviously complicates the procedure and subjects the assistant to exposure to blood and debris resulting from the procedure, particularly during the reaming operation.

Referring to FIGS. 11 to 15, there is shown a self-retaining protective retractor device generally denoted 24 in accordance with a preferred embodiment of the invention. As best can best be seen in FIG. 15 the retractor device 24 includes a planar protector element or pad 26 comprising a enlarged oval portion 28a which narrows down to a distal end portion 28b. In general, oval portion 28a lies flat on the patent and is used to protect the parts of the patient's body adjacent the incision, while narrow portion 28b extends into the incising and protects the deeper muscles. End portion 28b includes a spike or spikes 30 thereon which keep the retractor 24 from slipping once tensioned in the manner to be described. Oval portion 28a includes an elongate longitudinally extending slot 32 therein having a keyhole opening 32a at one end.

Figure 11:
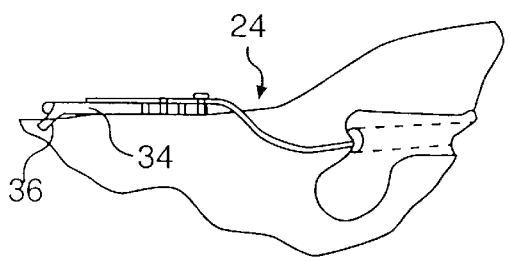
FIGS. 11 and 12 are a schematic side elevation view and top plan view, respectively, showing a protective retractor device according to the invention in place on a patient.
Figure 12:
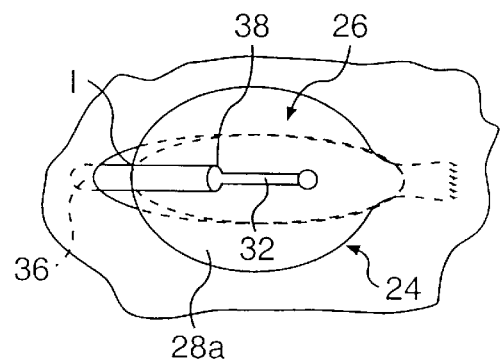
Figure 13:
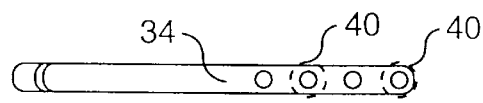
FIGS. 13 and 14 are a top plan view and a side elevational view, respectively, of the tensioning arm of the protective retractor device of FIGS. 11 and 12.
Figure 15:
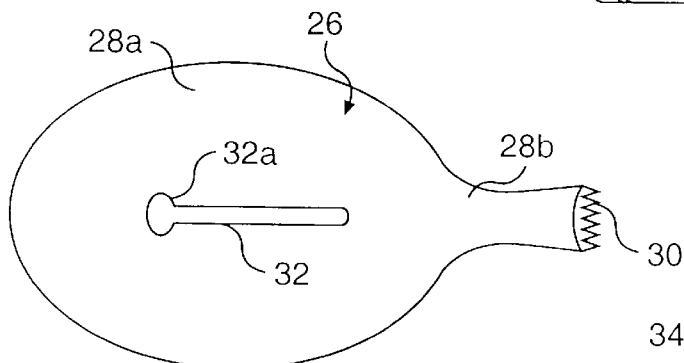
FIG. 15 is a top plan view of the protective pad of the protective retractor device of FIGS. 11 and 12.
Figure 14:
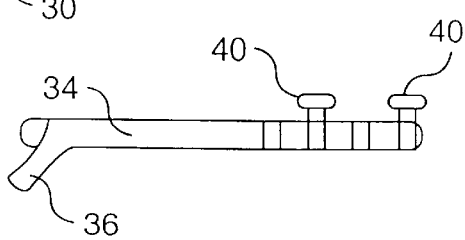

As shown in FIGS. 13 and 14, retractor device 24 also includes an elongate tensioning arm 34 having a hook 36 at the proximal end thereof adapted to engage the proximal end of an incision I as shown in FIG. 12 (and is also indicated in FIG. 11). A removable post 38, which includes an enlarged head and is shaped so as to fit through keyhole 32a, is located at the distal end of tensioning arm 34. As perhaps can be best seen in FIGS. 13 and 14, tensioning arm 34 includes a series of openings or screw holes 40 along a portion of the length thereof which enable the longitudinal position of post 38 to be varied. By tightening down on post 40, the oval portion 28a of protective retractor device 24 can be clamped in place, and with spike or spikes 30 secured to the bone, and hook 36 hooked into the incision, the overall device 24 is self-retaining. The location or position of clamping post can be varied to clamp the protective pad 28a at different points along slot 32 depending on the related "geometry" of the surgical wound site (e.g., the length or size of the incision, the location thereof relative to the bone, etc.). Tensioning arm 34 also serves to stretch the skin enough to support the weight of the protective retractor pad 26 while the adjustment mechanism, provided by positionable clamping post 40, enables rapid insertion and repositioning of the device.

As discussed above, the self-retaining retractor device 24, which can be made of metal, plastic and any other approved material, is used to protect the soft tissue during intermedullary reaming and thus can be installed prior to the reaming steps shown in FIGS. 4(c) and 4(d) above. The device 24 is easily inserted, tensioned, and adjusted and is readily removed and cleaned. Because of this, the device can reduce surgical time as compared with prior art devices designed for the same or similar purposes.

Although the present invention has been described relative to specific exemplary embodiments thereof, it will be understood by those skilled in the art that variations and modifications can be effected in these exemplary embodiments without departing from the scope and spirit of the invention.

What is claimed:

1. A guide pin for use in fixation of a fractured bone by the surgical placement of an intermedullary rod, said pin comprising:
   a curved pin member adapted for use as a guide pin for a reamer in surgical placement of an intermedullary rod, said pin member being of a substantially smaller size than the intermedullary rod to be introduced by surgical placement and having a radius of curvature between one and seven inches, said pin member further including a proximal end, and a sharp distal end adapted to be driven into a bone to be fixated by repeated impacts on the proximal end of the curved pin member.

2. A guide pin as claimed in claim 1 wherein said curved pin member is tapered over at least a portion of the length thereof between said proximal end and said distal end.

3. A guide pin as claimed in claim 2 wherein said curved pin member includes fluting at the proximal end thereof.

4. A guide pin as claimed in claim 2 wherein said pin member includes an enlarged head at the proximal end thereof.

5. A guide pin as claimed in claim 1 wherein said sharp distal end of said curved pin member is symmetrical in cross section and has a symmetrically disposed tip.

6. A guide pin as claimed in claim 1 wherein said curved pin member has an outer radius and an inner radius shorter than said outer radius and said sharp distal end includes an asymmetrical tip located closer to said inner radius than said outer radius so that a path followed by said pin member in response to said repeated impacts on the proximal end thereof tends to increase in curvature.

7. A guide pin as claimed in claim 6 wherein said pin member has a radius of curvature between five and seven inches.

8. A guide pin as claimed in claim 1 wherein said curved pin member has an outer radius and inner radius shorter than said outer radius and said sharp distal end includes an asymmetrical tip located closer to said outer radius that said inner radius so that a path followed by said pin member tends to straighten in response to said repeated impacts on the proximal end thereof.

9. A guide pin as claimed in claim 8 wherein said pin member has a radius of curvature of from one to three inches and is adapted for use in fixation of small bones.

10. A guide pin for use in fixation of a fractured bone, said pin comprising:
    a curved pin member of a radius of curvature between one and seven inches and including a proximal end, and a sharp distal end adapted to be driven into a bone to be fixated by repeated impacts on the proximal end of the curved pin member, said curved pin member having an outer radius and an inner radius shorter than said outer radius and said sharp distal end including an asymmetrical tip located closer to said outer radius that said inner radius so that a path followed by said pin member tends to straighten in response to said repeated impacts on the proximal end thereof.

11. In a combination, a pin guide device and a guide pin for use in fixation of a fractured bone, said pin guide device having a hollow curved pin guide portion and said guide pin being received in said pin guide portion and having a radius of curvature in said pin guide portion of between one and seven inches, said guide pin having a proximal end and a sharp distal end adapted to be driven into a bone to be fixated by repeated impacts on the proximal end of the curved pin member.

12. A method of fixating a small bone having a fracture therein, comprising:
    providing a curved pin element having a radius of curvature of between one and three inches; and
    driving the pin element into the small bone to provide fixation of the fracture,
    said pin element including an enlarged proximal head portion, and said pin element being driven into the small bone by repeated impacts on said head portion.

13. A method as claimed in claim 12 wherein said pin element includes an enlarged proximal end portion and said pin element is driven into the small bone by repeated impacts on said head portion.

14. A method as claimed in claim 12 wherein said method further comprises using a pin guide device having a hollow curved pin guide portion in placing the pin element at a desired entry point on the small bone.

15. A method as claimed in claim 14 wherein at least said pin guide portion of said pin guide device comprises separable portions and said method further comprises placing the distal end of said pin guide portion against the small bone at the desired entry point, inserting the pin element through said pin guide portion and hammering the pin element into the bone, separating the separable portions of said guide device to free the pin from the device and thereafter hammering the pin further into the bone to provide said fixation.

16. A method of preparing a fractured bone of a patient for the introduction of an intermedullary rod for fixating the bone, said method comprising:

creating an entry incision through soft tissue adjacent to an end portion of the fractured bone into which intermedullary rod is to be inserted;

driving a curved guide pin into the bone so that the guide pin at least penetrates into the medullary canal;

placing a protective retractor device over an area of the patient adjacent to the bone;

disposing a flexible reamer element over said curved guide pin; and using the curved guide pin as a guide, reaming out the bone along the length of the guide pin to create a reamed opening into the medullary canal.

17. A method as claimed in claim 16 further comprising capturing said guide pin with said flexible reamer and thereafter removing the reamer with the guide pin captured thereby.

18. A method as claimed in claim 17 wherein said method further comprises using a pin guide device to guide the curved guide pin to a desired entry point on the bone prior to driving the pin into bone.

19. A method as claimed in claim 18 wherein said pin guide device includes a curved guide portion having a distal end and said method further comprises inserting said curved guide pin through said curved guide portion and hammering said pin into the bone, removing the guide device and hammering the pin further into the bone in preparation for said reamer.

20. A method as claimed in claim 16 wherein said placing of said protective retractor device includes placing a protective pad portion of the retractor device over said area, securing a distal end of the retractor device to the bone, and using a tensioning arm of the retractor device to further secure the device in place.

21. A method as claimed in claim 20 wherein the step of using of said tensioning arm to secure the retractor device in place includes engaging the tissue at one end of the entry incision with one end of the tensioning arm and clamping the pad to the arm.

22. A method of preparing a fractured bone of a patient for the introduction of an intermedullary rod for fixating the bone, said method comprising:

creating an entry incision through soft tissue adjacent to an end portion of the fractured bone into which the intermedullary rod is to be inserted;

driving a curved guide pin through the entry incision into the bone so that the guide pin at least penetrates into the medullary canal;

disposing a flexible reamer element over the curved guide pin; and using the curved guide pin as a guide, using the reamer element to ream out the bone along the length of the guide pin to create a reamed opening into the medullary canal.

23. A method as claimed in claim 22 further comprising capturing said guide pin with said flexible reamer and thereafter removing the reamer with the guide pin captured thereby.

24. A method as claimed in claim 23 wherein said method further comprises using a pin guide device to guide the curved guide pin to a desired entry point on the bone prior to driving the pin into bone.

25. A method as claimed in claim 24 wherein said pin guide device includes a curved guide portion having a distal end, and said method further comprises inserting said curved guide pin through said curved guide portion and hammering said pin into the bone, removing the guide device, and hammering the pin further into the bone in preparation for said reamer.

26. A method of fixating a small bone having a fracture therein, said method comprising:

using a pin guide device having a hollow curved pin guide portion in placing a curved pin element having a radius of curvature of between one and three inches at a desired entry point on the small bone;

driving the pin element into the small bone to provide fixation of the fracture.

27. A method as claimed in claim 26 wherein at least said pin guide portion of said pin guide device comprises separable portions and said method further comprises placing the distal end of said pin guide portion against the small bone at the desired entry point, inserting the pin element through said pin guide portion and hammering the pin element into the bone, separating the separable portions of said guide device to free the pin from the device, and thereafter hammering the pin further into the bone to provide said fixation.

* * * * *